United States Patent
Yanaka et al.

Patent Number: 5,637,586
Date of Patent: Jun. 10, 1997

[54] BENZIMIDAZOLESULFONAMIDE DERIVATIVES AND PHARMACEUTICAL COMPOSITION

[75] Inventors: Mikiro Yanaka, Chiba; Hiroyuki Enari, Tokyo; Toshikazu Dewa, Tokyo; Toru Yamazaki, Tokyo, all of Japan

[73] Assignee: Kureha Chemical Industry Co., Ltd., Tokyo, Japan

[21] Appl. No.: 511,155

[22] Filed: Aug. 4, 1995

[30] Foreign Application Priority Data

Aug. 11, 1994 [JP] Japan .................. 6-210373

[51] Int. Cl.⁶ .................. A61K 31/54; C07D 417/02
[52] U.S. Cl. .................. 514/228.2; 514/234.5; 514/253; 544/62; 544/370; 544/139
[58] Field of Search .................. 514/228.2, 234.5, 514/253; 544/62, 370, 139

[56] References Cited

U.S. PATENT DOCUMENTS

| | | | |
|---|---|---|---|
| 4,880,804 | 11/1989 | Carini et al. | 514/234.5 |
| 5,137,909 | 8/1992 | Chiu et al. | 514/394 |
| 5,336,681 | 8/1994 | Imaki et al. | 514/347 |
| 5,399,578 | 3/1995 | Buhlmayer et al. | 514/381 |

FOREIGN PATENT DOCUMENTS

| | | |
|---|---|---|
| 0392317 | 10/1990 | European Pat. Off. |
| 0400835 | 12/1990 | European Pat. Off. |

OTHER PUBLICATIONS

Chemical Abstracts, The American Chemical Society, vol. 58, No. 4, Feb. 18, 1963, pp. 1963.
Carini et al., Nonpeptide Angiotensin II Receptor Antagonists, J. Med. Chem., 34, 2525–2547 1991.

*Primary Examiner*—Joseph McKane
*Assistant Examiner*—Richard S. Myers, Jr.
*Attorney, Agent, or Firm*—Sughrue, Mion, Zinn, Macpeak & Seas

[57] ABSTRACT

A benzimidazolesulfonamide derivative of the formula (I):

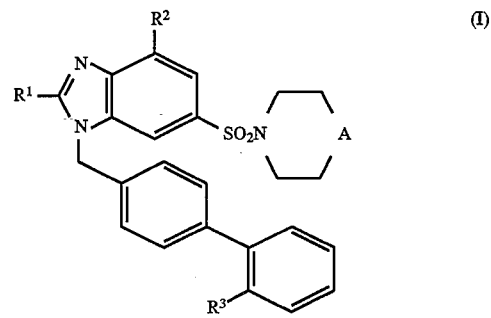

wherein $R^1$ is an alkyl group of 1 to 6 carbon atoms or a haloalkyl group of 1 to 6 carbon atoms; $R^2$ is a hydrogen atom, an alkyl group of 1 to 6 carbon atoms, a haloalkyl group of 1 to 6 carbon atoms, $-OR^4$, $-O(CH_2)_m C_6H_5$, $-(CH_2)_n C_6H_5$, $-NH_2$, $-NHR^5$, $-NHC(=O)R^6$, $-N(R^7)_2$, $-NHC(=O)(CH_2)_p C_6H_5$, or $-NHC(=O)CH(C_6H_5)_2$; $R^3$ is an azole group, $-COOH$, $-COOR^8$, or $-SO_3H$; A is $-O-$, $-NH-$, or $-S(O)_q-$; $R^4$, $R^5$, $R^6$, $R^7$, and $R^8$ are independently an alkyl group of to 6 carbon atoms; m, n, and p are independently 0 or an integer of 1 to 6; and q is 0, 1, or 2, or a salt thereof; and a pharmaceutical composition comprising the above compound are disclosed. The compound exhibits a stable and strong antagonism to angiotensin II.

6 Claims, No Drawings

BENZIMIDAZOLESULFONAMIDE DERIVATIVES AND PHARMACEUTICAL COMPOSITION

BACKGROUND OF THE INVENTION

1. Field of the Invention

The present invention relates to a benzimidazolesulfonamide derivative or a salt thereof, and a pharmaceutical composition, particularly, an angiotensin II antagonist, containing said benzimidazolesulfonamide derivative or a pharmaceutically acceptable salt thereof.

2. Description of the Related Art

An angiotensin II is an octapeptide hormone having an activity to raise blood pressure. Increase of the hormone production causes hypertension or central nervous system diseases. Thus, it is known that inhibition of production or function of the angiotensin II is effective in the treatment for such diseases.

A renin inhibitor and an angiotensin converting enzyme (ACE) inhibitor which inhibit the production of the angiotensin II have been developed as an angiotensin II inhibitor. However, there are questions that these inhibitors cannot control the angiotensin II produced by enzymes other than renin and ACE, and that they affect other metabolic pathways.

The angiotensin II performs its function by the interaction with a particular receptor present in the cell membrane. Therefore, an antagonist of the angiotensin II receptor is greatly desired as an agent for inhibiting the action of all the produced angiotensin II at the receptor site without affecting other metabolic pathways, i.e., an agent which is more specific and hardly exhibits side effects.

As the angiotensin II receptor antagonist, for example, peptide analogues such as Saralasin were reported. However, its application is limited, because the antagonism thereof is not sufficient and does not have oral adsorbability. Non-peptide antagonists of the angiotensin II receptor were recently reported as an agent to remedy such defects. As an example thereof, 2-butyl-4-chloro-5-(hydroxymethyl)-1-[[2'-(1H-tetrazol-5-yl)biphenyl-4-yl]methyl]imidazole (DuP753: Du Pont) (J. Med. Chem., 34: 2525–2547, 1991) is known. However, compounds exhibiting the stronger angiotensin II antagonism have been desired increasingly.

Meanwhile, as benzimidazole derivatives, compounds described in Merck's EP Publication No. 400,835 [corresponding to Japanese Unexamined Patent Publication (Kokai) No. 3-27362], compounds described in EP Publication No. 392,317 [corresponding to Japanese Unexamined Patent Publication (Kokai) No. 3-63264: THOMAE K GmbH], and compounds described in Du Pont's U.S. Pat. No. 5,137,906 are known. However, the chemical structures of the above compounds are different from that of the benzimidazolesulfonic acid cyclic amide derivative of the present invention. It is believed that benzimidazole compounds are suitable, by virtue of pharmacological effects thereof, to treat diseases such as hypertension, heart failure, ischemic peripheral circulatory disorder, myocardial ischemia, diabetic nephropathy, glaucoma, and gastoenteropathy, and disease of urinary bladder, or prevent progression of heart failure after cardiac infarction.

SUMMARY OF THE INVENTION

Under the circumstances, the inventors of the present invention searched a wide range of compounds, and as a result, discovered that a novel benzimidazolesulfonamide derivative having a cyclic amide group, or a pharmaceutically acceptable salt thereof, exhibits a stabler and stronger antagonism to angiotensin II than those of known compounds, and then, completed the present invention.

Accordingly, the present invention relates to a benzimidazolesulfonamide derivative of the formula (I) (hereinafter, sometimes referred to as "the compound of the present inventions"):

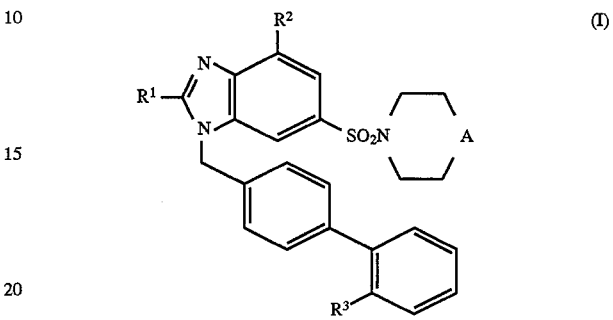

wherein $R^1$ is an alkyl group of 1 to 6 carbon atoms, or a haloalkyl group of 1 to 6 carbon atoms; $R^2$ is a hydrogen atom, an alkyl group of 1 to 6 carbon atoms, a haloalkyl group of 1 to 6 carbon atoms, —$OR^4$, —$O(CH_2)_mC_6H_5$, —$(CH_2)_nC_6H_5$, —$NH_2$, —$NHR^5$, —$NHC(=O)R^6$, —$N(R^7)_2$, —$NHC(=O)(CH_2)_pC_6H_5$, or —$NHC(=O)CH(C_6H_5)_2$; $R^3$ is an azole group, —COOH, —$COOR^8$, or —$SO_3H$; A is —O—, —NH—, or —$S(O)_q$—; $R^4$, $R^5$, $R^6$, $R^7$, and $R^8$ are independently an alkyl group of 1 to 6 carbon atoms; m, n, and p are independently 0 or an integer of 1 to 6; and q is 0, 1, or 2, or a salt thereof, particularly, a pharmaceutically acceptable salt thereof.

Further, the present invention also relates to a pharmaceutical composition comprising the benzimidazolesulfonamide derivative of the formula (I) or a pharmaceutically acceptable salt thereof and a pharmaceutically acceptable carrier or diluent.

DETAILED DESCRIPTION OF THE PREFERRED EMBODIMENTS

Generally, it is known that sulfonamide compounds are hard to be hydrolyzed in comparison with carboxylic amide compounds (Morison, R. T. and Boyd, R. N., Organic Chemistry, page 1181, 1985) [Japanese fourth edition, translated by Nakanishi, K. Kurono, M., and Nakadaira, Y., Tokyo kagaku dojin, 1985]. Further, it is known that sulfonamide compounds are hard to be metabolized in enzyme reactions such as hydroxidation (Drug Metab. Dispos., 9: 476–480, 1981). Thus, the benzimidazolesulfonic acid cyclic amide derivatives according to the present invention are apparently hard to be metabolized in vivo, and may stably exhibit the angiotensin II receptor antagonism.

The term "alkyl of 1 to 6 carbon atoms" used herein includes, for example, a methyl, ethyl, n-propyl, i-propyl, n-butyl, i-butyl, s-butyl, t-butyl, n-pentyl, i-pentyl, neopentyl, t-pentyl, n-hexyl, i-hexyl, or t-hexyl group, but a methyl, ethyl, n-propyl, or n-butyl group is preferable.

The haloalkyl group of 1 to 6 carbon atoms is a group carrying 1 to 9 halogen atoms (one or more kinds, preferably, one kind, more preferably, of halogen atoms) such as a chlorine, bromine, fluorine or iodine atom on the above alkyl group of 1 to 6 carbon atoms. Examples are a halomethyl, haloethyl, halopropyl, and halobutyl group. The preferred haloalkyl group is, for example, a trifluoromethyl, or n-nonafluorobutyl group.

The azole group is a 5-membered ring group containing 2 to 4 hetero atoms, such as a nitrogen, oxygen or sulfur atom, such as a group of imidazole, oxazole, thiazole, pyrazole, isoxazole, isothiazole, triazole, oxadiazole, thiadiazole, tetrazole, oxatriazole, or thiatriazole. The preferred azole group is, for example, 1H-tetrazol-5-yl.

The sulfonamido group in the present invention is a 6-membered cycloaliphatic amido group having a hetero atom at the 4-position. The hetero atom at the 4-position is —O—, —NH—, —S—, —S(O)—, or —S(O)$_2$—. The preferred sulfonamido group is morpholino wherein the hetero atom is —O—, 1-piperazinyl wherein the hereto atom is —NH—, or thiomorpholino wherein the hetero atom is —S—.

The compound of the formula (I) wherein $R^1$ is a methyl, ethyl, n-propyl, n-butyl, trifluoromethyl, or n-nonafluorobutyl group; $R^2$ is a hydrogen atom, a methyl, ethyl, or trifluoromethyl group, or —OC$_6$H$_5$, —NHC(=O)(CH$_2$)$_n$C$_6$H$_5$, or —NHC(=O)CH(C$_6$H$_5$)$_2$ group; $R^3$ is 1H-tetrazol-5-yl, —COOH, or —COOR$^8$ wherein $R^8$ is an alkyl group of 1 to 4 carbon atoms; A is —O—, —NH—, or —S(O)$_q$—; q is 0, 1, or 2; and n is 0 or an integer of 1 to 4, or a salt thereof is preferable.

The salt of the compound of the present invention includes a salt with an inorganic or organic acid or a salt with an inorganic or organic base, preferably a pharmaceutically acceptable salt. As an acid addition salt, there may be mentioned, for example, hydrochloride, sulfate, methanesulfonate or p-toluenesulfonate; a salt with a dicarboxylic acid, such as oxalic, malonic, succinic, maleic or fumaric acid; or a salt with a monocarboxylic acid, such as acetic, propionic or burytic acid. The inorganic base suitable to form a salt of the compound of the present invention is, for example, a hydroxide, carbonate or bicarbonate of ammonium, sodium, lithium, calcium, magnesium or aluminum. As the salt with the organic base, there may be mentioned, for example, a salt with a mono-, di- or tri-alkylamine, such as methylamine, dimethylamine or triethylamine; a salt with a mono-, di- or tri-hydroxyalkylamine, guanidine, N-methylglucosamine or amino acid.

As the typical examples of the compounds according to the present invention, the structures of Compounds No. 1 to 16 are shown in the following Table 1. The results of elemental and mass spectrometric analyses thereof are listed in Table 2. The compounds listed in the following Tables 1 and 2 are sometimes referred to the numbers in the following Tables. In the following Tables, Me is methyl, Et is ethyl, Pr is propyl, Bu is butyl, Pen is pentyl, Ph is phenyl, and CN$_4$H is 1H-tetrazol-5-yl.

TABLE 1

| No. | $R^1$ | $R^2$ | $R^3$ | A | Molecular formula |
|---|---|---|---|---|---|
| 1 | nBu | H | 2-CN$_4$H | O | C$_{29}$H$_{31}$N$_7$O$_3$S |
| 2 | nBu | H | 2-CN$_4$H | S | C$_{29}$H$_{31}$N$_7$O$_2$S$_2$ |
| 3 | nBu | H | 2-CN$_4$H | NH | C$_{29}$H$_{32}$N$_8$O$_2$S |
| 4 | Me | H | 2-CN$_4$H | O | C$_{26}$H$_{25}$N$_7$O$_3$S |
| 5 | Et | H | 2-CN$_4$H | O | C$_{27}$H$_{27}$N$_7$O$_3$S |
| 6 | nPr | H | 2-CN$_4$H | O | C$_{28}$H$_{29}$N$_7$O$_3$S |
| 7 | nPen | H | 2-CN$_4$H | O | C$_{30}$H$_{33}$N$_7$O$_3$S |
| 8 | nBu | H | 2-COOH | O | C$_{29}$H$_{31}$N$_3$O$_5$S |
| 9 | nBu | H | 2-COOMe | O | C$_{30}$H$_{33}$N$_3$O$_5$S |
| 10 | nBu | Me | 2-CN$_4$H | O | C$_{30}$H$_{33}$N$_7$O$_3$S |
| 11 | nBu | CF$_3$ | 2-CN$_4$H | O | C$_{30}$H$_{30}$N$_7$O$_3$SF$_3$ |
| 12 | nBu | OPh | 2-CN$_4$H | O | C$_{35}$H$_{35}$N$_7$O$_4$S |
| 13 | nBu | NHCOCH$_2$Ph | 2-CN$_4$H | O | C$_{37}$H$_{38}$N$_8$O$_4$S |
| 14 | nBu | NHCO(CH$_2$)$_2$Ph | 2-CN$_4$H | O | C$_{38}$H$_{40}$N$_8$O$_4$S |
| 15 | nBu | NHCO(CH$_2$)$_3$Ph | 2-CN$_4$H | O | C$_{39}$H$_{42}$N$_8$O$_4$S |
| 16 | nBu | NHCOCHPh$_2$ | 2-CN$_4$H | O | C$_{43}$H$_{42}$N$_8$O$_4$S |

TABLE 2

| | | | Elemental analysis | | | | | |
|---|---|---|---|---|---|---|---|---|
| | | | Calculated | | | Found | | |
| No. | Molecular weight | Mass spectrum | C(%) | H(%) | N(%) | C(%) | H(%) | N(%) |
| 1 | 557.67 | 557(FAB) | 62.46 | 5.60 | 17.58 | 62.57 | 5.78 | 17.69 |
| 2 | 573.73 | 573(FAB) | 60.71 | 5.45 | 17.09 | 60.38 | 5.70 | 16.76 |
| 3 | 556.69 | 556(FAB) | 62.57 | 5.79 | 20.13 | 62.90 | 5.56 | 20.46 |
| 4 | 515.59 | 515(FAB) | 60.57 | 4.89 | 19.02 | 60.72 | 4.76 | 19.17 |
| 5 | 529.62 | 529(FAB) | 61.23 | 5.14 | 18.51 | 61.17 | 5.24 | 18.45 |
| 6 | 543.65 | 543(FAB) | 61.86 | 5.38 | 18.03 | 61.99 | 5.38 | 18.16 |
| 7 | 571.70 | 571(FAB) | 63.03 | 5.82 | 17.15 | 63.40 | 5.92 | 17.52 |
| 8 | 533.64 | 533(EI) | 65.27 | 5.86 | 7.87 | 65.35 | 5.78 | 7.95 |
| 9 | 547.67 | 547(EI) | 65.79 | 6.07 | 7.67 | 65.94 | 6.34 | 7.82 |
| 10 | 571.70 | 571(FAB) | 63.03 | 5.82 | 17.15 | 62.92 | 5.79 | 17.04 |
| 11 | 625.67 | 625(FAB) | 57.59 | 4.83 | 15.67 | 57.65 | 4.86 | 15.73 |
| 12 | 649.77 | 649(FAB) | 64.70 | 5.43 | 15.09 | 65.04 | 5.31 | 15.43 |
| 13 | 690.82 | 690(FAB) | 64.33 | 5.54 | 16.22 | 64.30 | 5.69 | 16.19 |
| 14 | 704.85 | 704(FAB) | 64.75 | 5.72 | 15.90 | 65.04 | 5.81 | 16.19 |

TABLE 2-continued

| | Molecular | Mass | Elemental analysis | | | | | |
| | | | Calculated | | | Found | | |
| No. | weight | spectrum | C(%) | H(%) | N(%) | C(%) | H(%) | N(%) |
|---|---|---|---|---|---|---|---|---|
| 15 | 718.88 | 718(FAB) | 65.16 | 5.89 | 15.59 | 65.03 | 6.14 | 15.46 |
| 16 | 766.92 | 766(FAB) | 67.34 | 5.52 | 14.61 | 67.29 | 5.46 | 14.56 |

The compounds of the present invention may be prepared by a process known per se. The typical scheme which may be used to prepare the compounds of the present invention will be illustrated hereinafter.

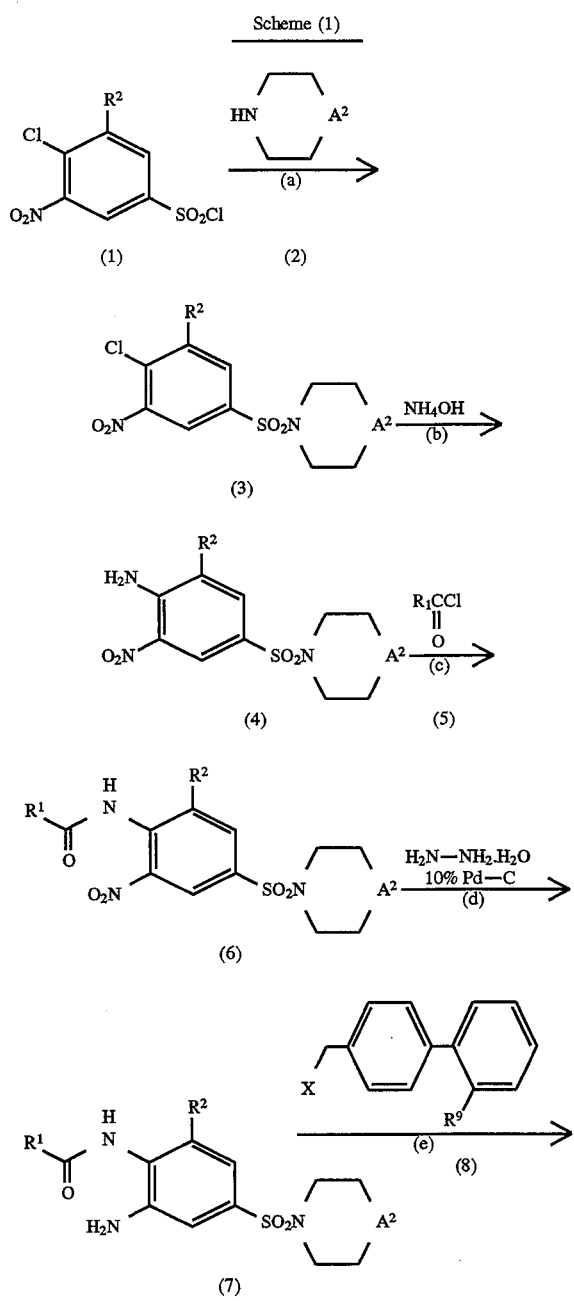

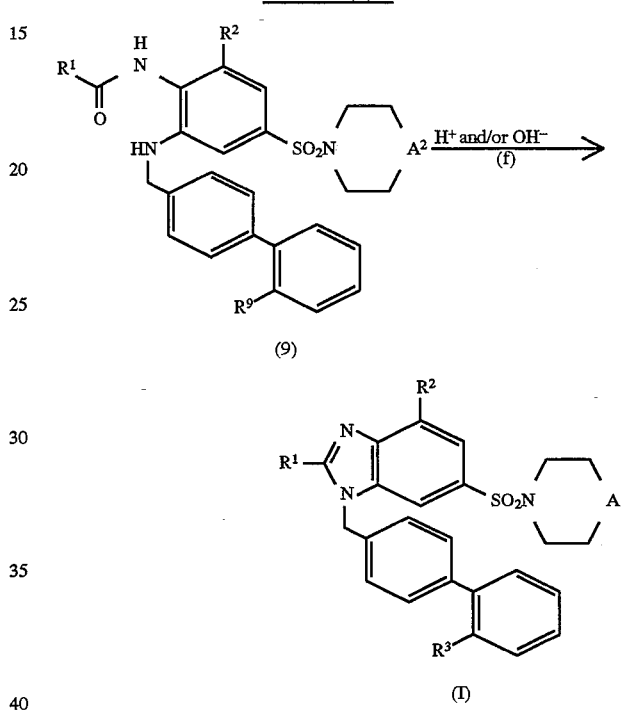

Each of the steps (a) to (f) in the above scheme will be illustrated hereinafter.

Step (a):

The compound of the formula (1) wherein $R^2$ has the same meaning as above is dissolved in an organic solvent, such as halogenomethane (for example, dichloromethane or chloroform). While cooling on ice, the solution is reacted with 2 to 3 equivalent amount of the cyclic amine of the formula (2) wherein $A^2$ is —O—, —S(O)$_q$—, or —NR$^5$—, q is 0, 1, or 2, and $R^5$ is t-butyldimethylsilyl group, to obtain the compound of the formula (3). It is preferable in this reaction to add dropwise a solution of the cyclic amine of the formula (2) in an organic solvent, such as halogenomethane.

The compound of the formula (1) may be prepared in accordance with the methods disclosed in known literatures, such as Chem. Ber., 24: 3190, 1891.

Step (b):

The compound of the formula (3) is dissolved in a cyclic ether (such as 1,4-dioxane) or a lower alcohol (such as methanol), and an aqueous ammonium solution is added to the solution. The reaction is performed at 50° to 120° C. to obtain the compound of the formula (4).

Step (c):

The compound of the formula (4) is dissolved in pyridine, and then reacted with the compound of the formula (5) wherein $R^1$ has the same meaning as above at 0° to 70° C., preferably after a base (such as dimethylaminopyridine) is added, to obtain the compound of the formula (6).

Step (d):

To a solution of the compound of the formula (6) in a lower alcohol (such as methanol or ethanol), a suspension of palladium/carbon in a lower alcohol is added. Then, the mixture is treated with hydrazine monohydrate to obtain the compound of the formula (7).

Step (e):

The compound of the formula (7) is dissolved in a halogenomethane, such as dichloromethane or chloroform, or an aromatic hydrocarbon, such as benzene or toluene, and an aliphatic tertiary amine, such as diisopropylethylamine, and the compound of the formula (8) [wherein X is a leaving group, such as $-OSO_2CH_3$, $-OSO_2C_6H_4-4-CH_3$, $-OSO_2CF_3$, or a halogen atom (such as a chlorine, iodine, or bromine atom), and $R^9$ is an optionally protected group $R^3$, i.e., 1-triphenylmethyl-1H-tetrazol-5-yl or $-CO_2R^8$, and $R^8$ has the same meaning as above] are added. The reaction is performed at 40° to 80° C. for 10 to 40 hours to obtain the compound of the formula (9).

The compound of the formula (8) wherein X is a bromine atom, and $R^9$ is 1-triphenylmethyl-1H-tetrazol-5-yl may be prepared in accordance with the methods disclosed in literatures, such as J. Med. Chem., 34: 2527–2547, 1991.

Step (f):

The compound of the formula (9) is dissolved in a cyclic ether such as tetrahydrofuran, and treated with hydrochloric acid at room temperature to obtain the compound of the formula (I).

Particularly, the compound of the formula (I) wherein $R^3$ is a carboxyl group may be prepared by evaporating the reaction solution to dryness after said treatment with hydrochloric acid, dissolving the residue in a cyclic ether such as tetrahydrofuran or a lower alcohol such as methanol or ethanol, and treating the solution with an alkaline aqueous solution.

The benzimidazolesulfonamide derivative of the formula (I) according to the present invention or a pharmaceutically acceptable salt thereof exhibits its pharmacological effects by antagonizing the angiotensin II receptor and blocking the action of angiotensin II. Accordingly, the present invention also relates to a pharmaceutical composition, particularly an angiotensin II antagonist comprising the above benzimidazolesulfonamide derivative of the formula (I) or the pharmaceutically acceptable salt as an effective ingredient, and a pharmaceutically acceptable carrier or diluent.

The compound of the present invention is effective as an agent for treating cardiovascular system diseases, for example, hypertension, cardiac disease, such as cardiac hypertrophy, heart failure, or cardiac infarction, or cerebral apoplexy, and central nervous system diseases. It is also effective as an agent for research in the role of the angiotensin II and its receptor in such diseases. The compound of the present invention may be administered to a mammal including human orally or parenterally such as percutaneously, intravenously or intraperitoneally.

The compound of the present invention was orally administered to mice at the dose of 500 mg/kg, but no death was observed during one week.

The compound of the present invention may be formulated by adding one or more pharmaceutically acceptable additives, to powder, tablet, granule, capsule, suppository, injection, or oral solution. As the additives, there may be mentioned, for example, magnesium stearate, talc, lactose, dextrin, starches, methylcellulose, fatty acid glycerides, water, propyleneglycol, low substituted hydroxypropylcellulose, carmelloses, povidone, polyvinylalcohol, or calcium stearate. Further, coloring agent, stabilizer, antioxidant, preservative, pH adjusting agent, isotonicity, solubilizing agent and/or soothing agent may be contained, if necessary. The granule, tablet, or capsule may be coated with a coating base, such as hydroxypropylmethyl cellulose or hydroxypropylmethyl cellulose phthalate.

The compound of the present invention may be contained at an amount of 0.1 to 500 mg, preferably 1 to 100 mg in a dose unit. The daily dose of the compound of the present invention is 0.1 to 150 mg/kg body weight, preferably 1 to 100 mg/kg body weight. The dose may be administered once a day, or divided twice or 3 times a day. The dose may be appropriately selected with respect to symptom of the patient.

The benzimidazolesulfonamide derivative of the formula (I) according to the present invention or the pharmaceutically acceptable salt thereof is a novel compound having strong angiotensin II antagonism, and useful as an agent for treating cardiovascular system diseases, for example, hypertension, cardiac disease, or cerebral apoplexy, and central nervous system diseases.

EXAMPLES

The present invention now will be illustrated by, but by no means limited to, the following Examples.

Example 1

Preparation of 4-[(4-chloro-3-nitrobenzene) sulfonyl] morpholine (3-1) [Step (a)]

In dichloromethane (500 ml), 4-chloro-3-nitrobenzenesulfonylchloride (1-1) (50.0 g) was dissolved. The solution was cooled on ice. To the solution, a solution of morpholine (33.1 g) in dichloromethane (30 ml) was added dropwise over 1 hour. The mixture was stirred for 1 hour while cooling on ice and stirred at room temperature for 1 hour. The mixture was washed with distilled water and saturated brine. The organic layer was dried over anhydrous sodium sulfate, and the solvent was evaporated. The residue was purified by silica gel column chromatography (Kieselgel 60=1.5 kg, chloroform) to obtain the above-captioned compound (3-1) (56.6 g) as light yellow needle crystals.

Melting Point: 145.5°–148.0° C.

$^1$H-NMR (500 MHz, CDCl$_3$) δ: 3.08 (t, 4H), 3.78 (t, 4H), 7.77 (d, 1H), 7.88 (dd, 1H), 8.23 (d, 1H)

Example 2

Preparation of 4-[(4-amino-3-nitrobenzene) sulfonyl] morpholine (4-1) [Step (b)]

The compound (3-1) (5.00 g) prepared in Example 1 was dissolved in dioxane (70 ml). To the solution, 28% ammonia aqueous solution (50 ml) was added, and the mixture was reacted in a vessel made of pressure glass at 95° C. for 12 hours. The reaction mixture was extracted with chloroform (100 ml) three times. The organic layer was dried over anhydrous sodium sulfate, and the solvent was evaporated to obtain the above-captioned compound (4-1) (4.51 g) as yellow needle crystals.

Melting Point: 199.0°–200.0° C.

$^1$H-NMR (500 MHz, CDCl$_3$) δ: 3.03 (t, 4H), 3.76 (t, 4H), 6.51 (brs, 2H), 6.93 (d, 1H), 7.68 (dd, 1H), 8.55 (d, 1H)

Example 3

Preparation of 4-[(3-nitro-4-valeramidobenzene) sulfonyl] morphine (6-1) [Step (c)]

The compound (4-1) (22.8 g) prepared in Example 2 was dissolved in anhydrous pyridine (150 ml), and dimethylaminopyridine (11.6 g) was added to the solution. After the mixture was cooled on ice, valeryl chloride (5-1) (28.3 ml) was added dropwise to the solution over 30 minutes. The mixture was stirred at room temperature for 30 minutes, and further stirred at 60° C. for 27 hours. The reaction mixture was extracted with chloroform (200 ml) three times. The organic layer was dried over anhydrous sodium sulfate, and the solvent was evaporated. Toluene was added to the residue, and pyridine was removed by azeotropically distilling off. The crude product was purified by silica gel column chromatography (Kieselgel 60=2.0 kg, from chloroform to chloroform/methanol=40/1), and the resulting solid (24.9 g) was recrystallized from dichloromethane/hexane (2/1) to obtain the above-captioned compound (6-1) (20.1 g) as light yellow needle crystals.

Melting Point: 129.0°–130.0° C.

$^1$H-NMR (500 MHz, CDCl$_3$) δ: 0.98 (t, 3H), 1.45 (sext, 2H), 1.77 (quint, 2H), 2.55 (t, 2H), 3.05 (t, 4H), 3.76 (t, 4H), 7.96 (dd, 1H), 8.61 (d, 1H), 9.08 (d, 1H), 10.57 (brs, 1H)

Example 4

Preparation of 4-[(3-amino-4-valeramidobenzene) sulfonyl] morpholine (7-1) [Step (d)]

The compound (6-1) (10.1 g) prepared in Example 3 was dissolved in ethanol (750 ml), and the solution was heated at 55° C. After dissolved air was ceased to bubble, a suspension of 10% palladium/carbon (1.50 g) in ethanol (20 ml), and then hydrazine monohydrate (10 ml) were added to the solution. After the mixture was further heated for 5 minutes, the catalyst was filtered out through celite. The filtrate was concentrated to obtain the above-captioned compound (7-1) (8.49 g) as white foam.

$^1$H-NMR (500 MHz, CDCl$_3$) δ: 0.97 (t, 3H), 1.44 (brq, 2H), 1.75 (brt, 2H), 2.45 (t, 2H), 3.00 (t, 4H), 3.74 (t, 4H), 3.98 (brs, 2H), 7.16 (brs, 1H), 7.18 (s, 1H), 7.52 (d, 1H)

Example 5

Preparation of 4-[[3-[[2'-(1-triphenylmethyltetrazol-5-yl) biphenyl-4-yl]methylamino]-4-valeramidobenzene] sulfonyl]morpholine (9-1) [Step (e)]

The compound (7-1) (8.49 g) prepared in Example 4 was dissolved in anhydrous chloroform (200 ml). To the solution, N-(triphenylmethyl)-5-[4'-(bromomethyl) biphenyl-2-yl]tetrazole (8-1) (13.9 g), and then diisopropylethylamine (9.70 g) were added. The mixture was stirred at 60° C. for 12 hours under a nitrogen gas atmosphere. After the reaction mixture was washed with distilled water, the organic layer was dried over anhydrous sodium sulfate, and the solvent was evaporated. The crude product was purified by silica gel column chromatography (Kieselgel 60=1 kg, chloroform/acetone=40/1) to obtain the above-captioned compound (9-1) (5.31 g) as a white solid.

$^1$H-NMR (500 MHz, CDCl$_3$) δ: 0.92 (t, 3H), 1.37 (brq, 2H), 1.70 (brt, 2H), 2.34 (brt, 2H), 2.77 (t, 4H), 3.59 (t, 4H), 4.24 (d, 2H), 4.54 (brs, 1H), 6.93–6.98 (m, 7H), 7.08–7.13 (m, 5H), 7.25–7.35 (m, 7H), 7.48–7.51 (m, 3H), 7.88 (d, 1H)

Example 6

Preparation of 4-[[2-n-butyl-1-[2'-[(1H-tetrazol-5-yl) biphenyl-4-yl]methyl]benzimidazol-6-yl]sulfonyl] morpholin (No. 1) [Step (f)]

The compound (9-1) (5.31 g) prepared in Example 5 was dissolved in tetrahydrofuran (50 ml). To the solution, concentrated hydrochloric acid (15 ml) was added, and the mixture was stirred at room temperature for 3 hours. The reaction mixture was adjusted to pH 4 with 10N NaOH aqueous solution, and extracted with chloroform (100 ml) three times. The organic layer was dried over anhydrous sodium sulfate, and the solvent was evaporated. The crude product was purified by silica gel column chromatography (Kieselgel 60=300 g, chloroform/methanol=15/1) to obtain the above-captioned Compound (No. 1) (2.97 g) as foam.

$^1$H-NMR(500 MHz, CDCl$_3$) δ: 0.94(t, 3H), 1.45(sext, 2H), 1.84(quint, 2H), 2.88(t, 2H), 2.91(t, 4H), 3.71(t, 4H), 5.38(s, 2H), 6.94(d, 2H), 7.08(d, 2H), 7.40(d, 1H), 7.45(d, 1H), 7.53–7.67(m, 3H), 7.68(d, 1H), 7.96(d, 1H)

Example 7

Acute toxicity

Five-week-old ICR female mice (5 mice per group) were bred for acclimation for a week. Then, the Compounds No. 1 to No. 16 of the present invention were dissolved or dispersed in a 0.5% methylcellulose aqueous solution, and orally administered to the mice in a single dosage (500 mg/kg). The number of deaths was observed for 6 days after the administration, but no death in each group was observed.

Example 8

Binding to receptors

In this Example, the affinity to the angiotensin II receptor subtype 1 or subtype 2 was evaluated by a binding assay in accordance with the method described in Biochem. Pharmacol., 33, 4057–4062 (1984).

Specifically, the measurement of the total binding in the presence of each drug was performed as follows:

A mixture (final volume=0.25 ml) of a drug in a given concentration (the drug was dissolved in dimethylsulfoxide, and diluted to a double volume with a buffer attached to a drug discovery system to prepare a sample for the assay; 0.025 ml), a tracer (0.025 ml), and receptors (0.2 ml) was incubated [in the case of the angiotensin II receptor subtype 1 (AT$_1$), at room temperature for 3 hours, and in the case of the subtype 2 (AT$_2$), at 37° C. for 1 hour]. Then, the reaction mixture was filtered with suction (GF/C filter was used in AT$_1$, and GF/B filter was used in AT$_2$). The filter papers after filtration with suction (the tracer bound to the receptors) were counted by a γ-well counter (ARC-500, Aloka). The non-specific bindings were measured by repeating the above method, except that a large excess amount of a displacer was added. The specific binding of the drug in the given concentration was calculated by subtracting the non-specific binding from the total binding, respectively.

In AT$_1$ and AT$_2$, the percentages to inhibit the bindings of radioactive ligands (tracer) to receptors by the drugs to be tested (binding inhibition % in 1 μM) were measured, using the drugs to be tested and control drugs in the given concentration. The results are shown in Table 3.

TABLE 3

| Compound | Binding inhibition % in 1 μM | |
|---|---|---|
| | AT$_1$ | AT$_2$ |
| Compound No. 1 | 100 | 0 |
| DuP753 | 95 | 0 |

TABLE 3-continued

| | |
|---|---|
| In $AT_1$, receptor: | from adrenal glands in rabbits |
| tracer: | $^3$H-angiotention II |
| control drug: | DuP753 |
| (displacer): | DuP753 |
| In $AT_2$, recepter: | from cerebellar cortex in bovine |
| tracer: | $^{125}$I-Tyr$^4$-angiotensin II |
| control drug: | angiotensin II (human) |
| (displacer): | angiotensin II (human) |

From Table 3, it is clear that the compound of the present invention exhibits angiotensin II antagonism superior to that of the conventional angiotensin II antagonist.

Example 10

The Compound No. 1 (10 mg) of the present invention, lactose (36 mg), corn starch (150 mg), microcrystalline cellulose (29 mg), and magnesium stearate (5 mg) were mixed, and tableted to prepare tablets (230 mg/tablet).

Although the present invention has been described with reference to specific embodiments, various changes and modifications obvious to those skilled in the art are deemed to be within the spirit, scope, and concept of the invention.

We claim:

1. A benzimidazolesulfonamide compound of the formula (I):

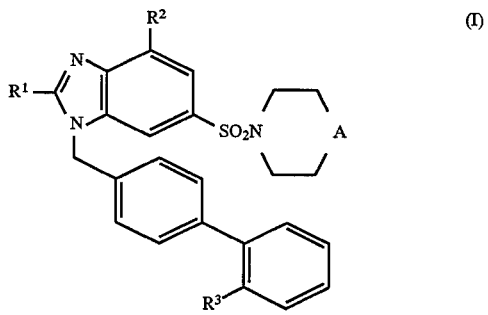

wherein $R^1$ is an alkyl group of 1 to 6 carbon atoms, or a haloalkyl group of 1 to 6 carbon atoms; $R^2$ is a hydrogen atom, an alkyl group of 1 to 6 carbon atoms, a haloalkyl group of 1 to 6 carbon atoms, —OR$^4$, —O(CH$_2$)$_m$C$_6$H$_5$, —(CH$_2$)$_n$C$_6$H$_5$, —NH$_2$, —NHR$^5$, —NHC(=O)R$^6$, —N(R$^7$)$_2$, —NHC(=O)(CH$_2$)$_p$C$_6$H$_5$, or —NHC(=O)CH(C$_6$H$_5$)$_2$; $R^3$ is an azole group, —COOH, —COOR$^8$, or —SO$_3$H; A is —O—, —NH—, or —S(O)$_q$—; $R^4$, $R^5$, $R^6$, $R^7$, and $R^8$ are independently an alkyl group of 1 to 6 carbon atoms; m, n, and p are independently 0 or an integer of 1 to 6; and q is 0, 1, or 2, or a salt thereof.

2. A benzimidazolesulfonamide compound according to claim 1, wherein $R^1$ is a methyl, ethyl, n-propyl, n-butyl, trifluoromethyl, or n-nonafluorobutyl group; $R^2$ is a hydrogen atom, a methyl, ethyl or trifluoromethyl group, or —OC$_6$H$_5$, —NHC(=O)(CH$_2$)$_p$C$_6$H$_5$, or —NHC(=O)CH(C$_6$H$_5$)$_2$; $R^3$ is 1H-tetrazol-5-yl, —COOH, or —COOR$^8$ wherein $R^8$ is an alkyl group of 1 to 4 carbon atoms; A is —O—, —NH—, or —S(O)$_q$—; p and q are independently 0, 1, or 2, or a salt thereof.

3. A pharmaceutical composition comprising a benzimidazolesulfonamide compound of the formula (I):

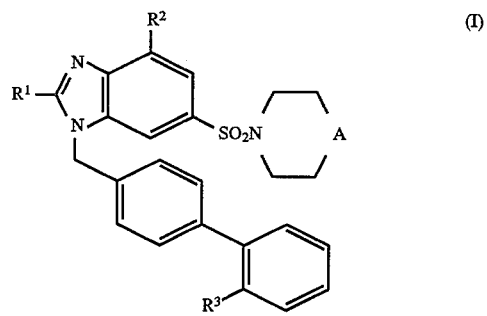

wherein $R^1$ is an alkyl group of 1 to 6 carbon atoms or a haloalkyl group of 1 to 6 carbon atoms; $R^2$ is a hydrogen atom, an alkyl group of 1 to 6 carbon atoms, a haloalkyl group of 1 to 6 carbon atoms, —OR$^4$, —O(CH$_2$)$_m$C$_6$H$_5$, —(CH$_2$)$_n$C$_6$H$_5$, —NH$_2$, —NHR$^5$, —NHC(=O)R$^6$, —N(R$^7$)$_2$, —NHC(=O)(CH$_2$)$_p$C$_6$H$_5$, or —NHC(=O)CH(C$_6$H$_5$)$_2$; $R^3$ is an azole group, —COOH, —COOR$^8$, or —SO$_3$H; A is —O—, —NH—, or —S(O)$_q$—; $R^4$, $R^5$, $R^6$, $R^7$, and $R^8$ are independently an alkyl group of 1 to 6 carbon atoms; m, n, and p are independently 0 or an integer of 1 to 6; and q is 0, 1, or 2, or a pharmaceutically acceptable salt thereof, and a pharmaceutically acceptable carrier.

4. A pharmaceutical composition according to claim 3, which is an angiotensin II receptor antagonist.

5. A pharmaceutical composition according to claim 3, which is an agent for treating a cardiovascular or central nervous system disease.

6. A method for treating a cardiovascular or central nervous system disease, comprising administering to a mammal in need thereof the compound according to claim 1 in a therapeutically effective amount.

* * * * *